United States Patent
Soya et al.

(10) Patent No.: US 11,116,732 B2
(45) Date of Patent: Sep. 14, 2021

(54) CAROTENOID-CONTAINING COGNITIVE FUNCTION IMPROVING COMPOSITION FOR USE IN EXERCISE THERAPY FOR IMPROVING COGNITIVE FUNCTION

(71) Applicants: ASTAREAL CO., LTD., Toyama (JP); UNIVERSITY OF TSUKUBA, Tsukuba (JP)

(72) Inventors: Hideaki Soya, Tsukuba (JP); Jangsoo Yook, Tsukuba (JP)

(73) Assignees: ASTAREAL CO., LTD., Nakaniikawa-gun (JP); UNIVERSITY OF TSUKUBA :, Tsukuba (JP)

( * ) Notice: Subject to any disclaimer, the term of this patent is extended or adjusted under 35 U.S.C. 154(b) by 0 days.

(21) Appl. No.: 16/666,088

(22) Filed: Oct. 28, 2019

(65) Prior Publication Data

US 2020/0060993 A1 Feb. 27, 2020

Related U.S. Application Data

(63) Continuation of application No. 16/308,364, filed as application No. PCT/JP2017/021203 on Jun. 7, 2017, now abandoned.

(30) Foreign Application Priority Data

Jun. 8, 2016 (JP) .................................. 2016-114468

(51) Int. Cl.
| | | |
|---|---|---|
| *A61K 31/122* | (2006.01) | |
| *A61K 31/015* | (2006.01) | |
| *A61K 36/05* | (2006.01) | |
| *A23L 33/10* | (2016.01) | |
| *A61P 25/00* | (2006.01) | |

(52) U.S. Cl.
CPC ............ *A61K 31/122* (2013.01); *A23L 33/10* (2016.08); *A61K 31/015* (2013.01); *A61K 36/05* (2013.01); *A61P 25/00* (2018.01); *A23V 2002/00* (2013.01)

(58) Field of Classification Search
CPC .... A61K 31/122; A61K 31/015; A61K 36/05; A23L 33/10
See application file for complete search history.

(56) References Cited

U.S. PATENT DOCUMENTS

| | | |
|---|---|---|
| 2006/0205826 A1 | 9/2006 | Romero et al. |
| 2007/0128310 A1 | 6/2007 | Honda et al. |
| 2009/0297492 A1 | 12/2009 | Satoh et al. |
| 2012/0171303 A1 | 7/2012 | Zanghi et al. |

FOREIGN PATENT DOCUMENTS

| | | |
|---|---|---|
| JP | 2006-116161 A | 5/2006 |
| JP | 2007-126455 A | 5/2007 |
| WO | WO 2011/031304 A2 | 3/2011 |

OTHER PUBLICATIONS

Byun et al., "Positive effect of acute mild exercise on executive function via arousal-related prefrontal activations: An fNIRS study", Neuroimage, vol. 98, 2014, pp. 336-345 (11 pages).
Erickson et al., "Exercise training increases size of hippocampus and improves memory", PNAS, vol. 108, No. 7, Feb. 15, 2011, pp. 3017-3022 (6 pages).
Intenational Search Report (Form PCT/ISA/210), dated Jul. 18, 2017, for International Application No. PCT/JP2017/021203.
Kim et al.,"Astaxanthin Improves Stem Cell Potency via an Increase in the Proliferation of Neural Progenitor Cells", Int. J. Mol. Sci., vol. 11, 2010, pp. 5109-5119 (11 pages).
Lu et al., "Astaxanthin rescues neuron loss and attenuates oxidative stress induced by amygdala kindling in adult rat hippocampus", Neurosci. Lett., vol. 591, 2015, pp. 49-53 (5 pages).
Yook et al., "Astaxanthin supplementation enhances adult hippocampal neurogenesis and spatial memory in mice", Mol. Nutr. Food Res., vol. 60, 2016, pp. 589-599 (11 pages).
Yook et al., "Tennen Yurai Supplement to Kaiba no Kino Sokushin", Tailku no Kagaku, vol. 65, No. 1, Jan. 1, 2015, pp. 21-27 (9 pages).
Extended European Search Report, dated Jan. 16, 2020, for European Application No. 17810371.9.
McCarty, "Practical Strategies for Preserving Good Cognitive Function into Old Age," http://www.nutriguard.com/Practical-Strategies-for-Preserving-Good-Cognitive-Function-into-Old-Age.pdf, May 31, 2013, pp. 1-56, XP055250488.
Satoh et al., "Preliminary Clinical Evaluation of Toxicity and Efficacy of a New Astaxanthin-rich Haematococcus pluvialis Extract," J. Clin. Biochem. Nutr., vol. 44. No. 3, May 2009 (Jan. 1, 2009), pp. 280-284, XP055647548.

*Primary Examiner* — Samira J Jean-Louis
(74) *Attorney, Agent, or Firm* — Birch, Stewart, Kolasch & Birch, LLP

(57) ABSTRACT

The present invention relates to a carotenoid-containing composition for use in exercise therapy for improving cognitive function, particularly exercise therapy for hippocampal neurogenesis.

7 Claims, 7 Drawing Sheets

A [Network 1]

B [Network 2]

CAROTENOID-CONTAINING COGNITIVE FUNCTION IMPROVING COMPOSITION FOR USE IN EXERCISE THERAPY FOR IMPROVING COGNITIVE FUNCTION

CROSS REFERENCE TO RELATED APPLICATIONS

This application is a Continuation of copending application Ser. No. 16/308,364, filed on Dec. 7, 2018, which is the National Phase under 35 U.S.C. § 371 of International Application No. PCT/JP2017/021203, filed on Jun. 7, 2017, which claims the benefit under 35 U.S.C. § 119(a) to Patent Application No. 2016-114468, filed in Japan on Jun. 8, 2016, all of which are hereby expressly incorporated by reference into the present application.

TECHNICAL FIELD

The present invention relates to a carotenoid-containing cognitive function improving composition for use in exercise therapy for improving cognitive function.

BACKGROUND ART

In recent years, among natural derived ingredients that are highly effective and safe for humans and have no side effects, development of brain food, in which the effect of enhancing brain function is considered to be clear in addition to the effects that are useful for maintaining the health of the body, has been attracted attention. Astaxanthin which is a carotenoid is a natural red pigment abundantly contained in crustaceans such as shrimps and crabs and salmon and is expected as a next generation natural supplement that provides a powerful antioxidant effect. Astaxanthin moves through the blood brain barrier into the brain.

In vitro, it has been reported that astaxanthin enhances the proliferation of neural progenitor cells (Non-Patent document 1). In addition, astaxanthin has been reported to protect against nerve injury due to epilepsy (Non-Patent document 2). However, the effect of astaxanthin on hippocampal function is unknown.

In the past, researches that investigated exercise effects on brain functions focused particularly on hippocampal function, which is responsible for memory and learning. In particular, in the dentate gyrus of the hippocampus, new neurons are born throughout the life (adult hippocampal neurogenesis; AHN), and they play an important role in memory formation by maturing this neoplastic cell in about 4 weeks and being incorporated into existing neural circuits. If adult hippocampal neurogenesis is suppressed by chronic stress and the like, it becomes a factor which causes depression and cognitive impairment.

It has been known that exercise increases the volume of the hippocampus and improves the memory ability not only in animals but also in humans (Non-Patent document 3). It has also been known that acute light exercise enhances the performance function through prefrontal cortex activity related to arousal (Non-Patent document 4).

In the research field of nutrigenomics, comprehensive analysis of gene expression using microarray has been carried out.

PRIOR ART DOCUMENTS

Non-Patent Documents

Non-Patent document 1: Kim J. H., Nam S. W., Kim B, W., Choi W. et al., Astaxanthin improves stem cell potency via an increase in the proliferation of neural progenitor cells. Int. J. mol. Sci. 2010, 11, 5109-5119

Non-Patent document 2: Lu Y., Xie T., He X. X., Mao Z. F. et al., Astaxanthin rescues neuron loss and attenuates oxidative stress induced by amygdala kindling in adult rat hippocampus. Neurosci. Lett. 2015, 597, 49-53.

Non-Patent document 3: Erickson K I, Voss M W, Prakash R S, Basak C, Szabo A, Chaddock L, Kim J S, Heo S, Alves H, White S M, Wojcicki T R, Mailey E, Vieira V J, Martin S A, Pence B D, Woods J A, McAuley E, Kramer A F. Exercise training increases size of hippocampus and improves memory. Proc Natl Acad Sci USA 108: 3017-3022, 2011.

Non-Patent document 4: Byun K, Hyodo K, Suwabe K, Ochi G, Sakairi Y, Kato M, Dan I, Soya. Positive effect of acute mild exercise on executive function via arousal-related prefrontal activations: an fNIRS study, Neuroimage 98: 336-345, 2014

SUMMARY OF THE INVENTION

Problems to be Solved by the Invention

The function of carotenoids, particularly astaxanthin, for exercise therapy to improve cognitive function, particularly for use in exercise therapy for brain, more specifically, hippocampal neurogenesis, has not been well known. An object of the present invention is to elucidate the function of carotenoids, particularly astaxanthin, for use in exercise therapy for improving cognitive function, particularly brain, more specifically, exercise therapy for hippocampal neurogenesis, and to find out new application of astaxanthin.

Means to Solve the Problems

As a result of intensive studies, the present inventors have found out that hippocampal neurons can be newly generated by using carotenoids, particularly astaxanthin in exercise therapy for improving cognitive function, particularly exercise therapy for hippocampal neurogenesis, whereby completed the present invention.

That is, the gist of the present invention is as follows.
[1] A carotenoid-containing cognitive function improving composition for use in exercise therapy for improving cognitive function.
[2] A carotenoid-containing memory function improving composition for use in exercise therapy for improving memory function.
[3] A carotenoid-containing learning function improving composition for use in exercise therapy for improving learning function.
[4] A carotenoid-containing hippocampal neurogenesis composition for use in exercise therapy for hippocampal neurogenesis.
[5] The composition according to any one of [1] to [4], wherein carotenoids is astaxanthin.
[6] The composition according to the above [5], wherein astaxanthin is derived from *Haematococcus* algae.
[7] The composition according to any one of the above [1] to [6], wherein it is for continuous ingestion for at least 4 weeks.
[8] The composition according to the above [1] to [7], wherein the exercise therapy is low intensity exercise therapy.
[9] The composition according to the above [8], wherein the low intensity exercise is an exercise of a ventilatory work threshold value or less.

[10] The composition according to any one of the above [1] to [9], wherein it is by upregulation of at least one gene selected from the group consisting of Igf1r, Lep and Cxcr4 genes.

[11] The composition according to the above [1] to [10], wherein it is a medicine or a food.

Effects of the Invention

According to the present invention, it can be provided a new use of carotenoids, in particular astaxanthin, for use in exercise therapy for improving cognitive function, particularly exercise therapy for improving memory and learning function, more particularly exercise therapy for hippocampal neurogenesis, which has never been known in the prior arts. The composition according to the present invention promotes hippocampal neurogenesis in a concentration-dependent manner, thereby improving cognitive function, in particular memory and learning functions.

EMBODIMENTS TO CARRY OUT THE INVENTION

Figure 1:
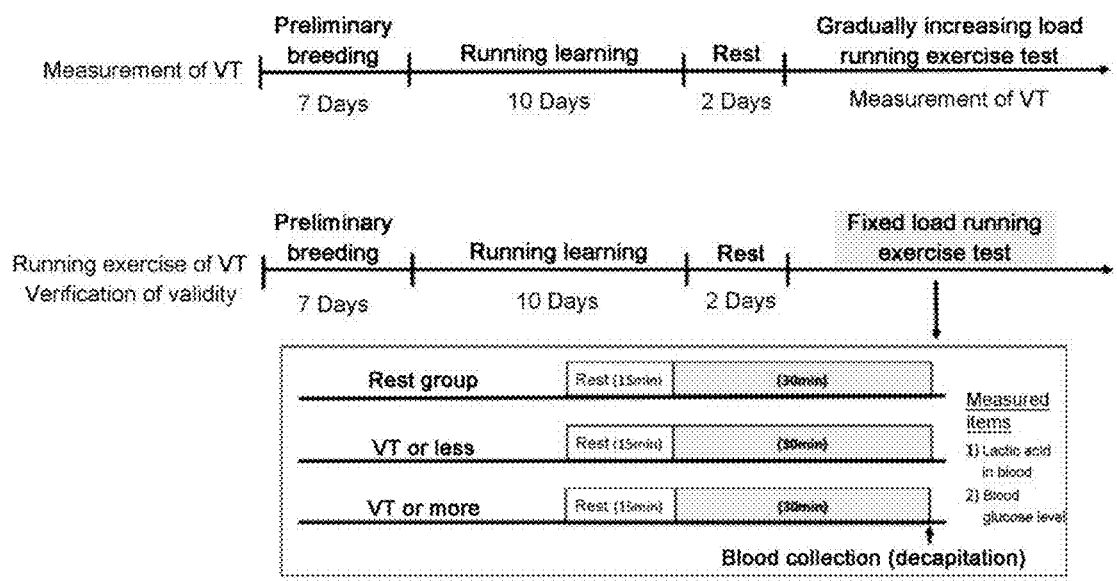
FIG. 1 shows experimental design in Example.

The present invention is to provide a carotenoid-containing hippocampal neurogenesis composition for use in exercise therapy for hippocampal neurogenesis.

The cognitive function in the present invention is a series of tasks for recognizing stimuli from internal and external environments, and defined to be comprehensive ability as intellectual activities such as perception, judgment, attention, memory, thought, language understanding.

Carotenoids are yellow to red pigments of terpenoids, including those derived from plants, algae and bacteria.

Examples of the carotenoid in the present invention include astaxanthin, actinioerythrol, bixin, canthaxanthin, capsanthin, capsorubin, β-8'-apo-carotenal (apocarotenal), β-12'-apo-carotenal, α-carotene, β-carotene, carotene (mixture of α- and β-carotenes), γ-carotene, β-cryptoxanthin, lutein, lycopene, biorelitrin, zeaxanthin, phytoene, phytofluene and esters thereof containing hydroxyl group or carboxyl group, etc., but the invention is not limited by these. The carotenoids in the present invention are preferably astaxanthin, lycopene, β-carotene, γ-carotene, phytofluene, phytoene, canthaxanthin, β-cryptoxanthin, capsanthin, lutein, zeaxanthin or fatty acid esters thereof, and most preferably astaxanthin.

The astaxanthin may be natural astaxanthin or synthetic astaxanthin. It is preferable that the astaxanthin is natural astaxanthin, more preferably it is derived from *Haematococcus* algae.

The natural astaxanthin is extracted from, for example, *Haematococcus* algae, specifically *Haematococcus pluvialis, Haematococcus lacustris, Haematococcus capensis, Haematococcus deroebakensis, Haematococcus zimbabwiensis*, etc., but the invention is not limited by these.

As the cultivating method of the above-mentioned *Haematococcus* algae, there may be mentioned various methods disclosed in JP Hei.8-103288A, etc., but the present invention is not limited to these methods, and it suffices that it is morphologically changed from a vegetative cell to a cyst cell that is a slumber cell.

The above-mentioned *Haematococcus* algae may be, if necessary, crushed its cell wall by the method disclosed in JP Hei.5-68585A, etc., and is extracted by adding an extraction solvent such as an organic solvent such as acetone, ether, chloroform and alcohol (ethanol, methanol, etc.), and carbon dioxide in supercritical state, etc.

*Haematococcus* algae extract consists mainly of astaxanthin and acylglycerol. The astaxanthin content in the *Haematococcus* algae extract is 3% by weight or more, preferably 3 to 40% by weight, and more preferably 5 to 12% by weight.

As a method for obtaining a high content of astaxanthin from *Haematococcus* algae, a closed-type culturing method free from contamination and propagation of heterologous microorganisms and less contamination of other contaminants is preferable, and can be obtained from a culture solution by a conventional method.

As astaxanthin or a starting material of astaxanthin of the composition of the present invention, commercially available products such as ASTOTS-S, ASTOTS-100, ASTOTS-ECS, ASTOTS-2.0PW, ASTOTS-3.0 MB (Registered Trademark) (Takeda Paper K. K., Chiba Prefecture), AstaReal oil 50F, AstaReal oil 5F, AstaReal powder 20F, water soluble AstaReal Liquid, AstaReal WS Liquid, AstaReal LOWS Liquid (Registered Trademark) (Fuji Chemical Industries Co., Ltd., Toyama Prefecture), BioAstin (Registered Trademark) (Toyo Koso Kagaku Co., Ltd., Chiba Prefecture), Astazine TM (BGG Japan Co., Ltd.), astaxanthin powder 1.5%, 2.5%, astaxanthin oil 5%, 10% (Bio Actives Japan Corporation), astaxanthin (*Oryza* Oil & Fat Chemical Co., Ltd.), SunActive AX (Registered Trademark) (Taiyo Kagaku Co., Ltd.) or *Haematococcus* WS30 (YAE-GAKI Bio-industry, Inc.), and the like can be also used.

As the synthetic astaxanthin, AstaSana (trademark) (DSM, Switzerland), Lucantin Pink (Registered Trademark) (BASF, Germany), etc. can also be used.

The astaxanthin content in the composition of the present invention is based on the weight converted into an astaxanthin free form.

The composition of the present invention should be ingested for at least 4 weeks and it is better to take it for a long period of time. In addition, it may be taken once per a day, but it may be divided into a plurality of times.

A content of the carotenoid, particularly astaxanthin, in the composition of the present invention can be contained, for example, in an amount of 0.01 to 99% by weight, preferably 0.1 to 90% by weight in a pharmaceutical product. Also, in the food and drink, it can be contained in an amount of 0.00001 to 10% by weight, preferably 0.0001 to 5% by weight.

An uptake amount of the astaxanthin for adults per a day may be 0.5 mg to 100 mg, preferably 1 mg to 30 mg in terms of the astaxanthin free body.

In the composition of the present invention, high spatial cognitive function can be exerted when the uptake period is longer, the content is higher or the daily uptake is higher.

The composition of the present invention is used in exercise therapy for hippocampal neurogenesis.

Exercise therapy for hippocampal neurogenesis in the present invention may be any exercise therapy, and, for example, therapy such as walking, jogging, marathon, bicycle, swimming, muscle training, stretching, ball game, skiing, tennis, stair climbing, etc., may be mentioned, and the present invention is not limited thereto.

During exercise, as the strength gets higher, the activity of muscle glycolysis is promoted, and pyruvic acid and lactic acid are produced from glycogen and glucose-6-phosphate (metabolite of glucose derived from blood). When lactic acid ($CH_3CHOHCOOH$) is generated, a hydrogen ion(s) is/are dissociated and it is bonded to bicarbonate ion(s) to form carbonic acid ($H_2CO_3$). This is dissociated into $H_2O$ and $CO_2$ by the catalytic action of carbonic anhydrase, and it is released outside the body through sweat, urine or exhalation gas, while on the other hand, it binds Na in the blood and is neutralized as sodium bicarbonate ($NaHCO_3$). At that time, since $CO_2$ in exhalation acts on the brainstem and stimulates ventilation, as compared with an increase in oxygen uptake ($VO_2$), an amount of ventilation and carbon dioxide discharge amount ($VCO_2$) are markedly increased. As a result of these metabolic-circulatory responses at the time of exercise, a threshold value in which $VCO_2$ is markedly increased relative to $VO_2$ is found. This is defined to be a ventilatory work threshold value (VT: ventilatory threshold) (Beaver W L, Wasserman K, Whipp B J. A New Method for Detecting Anaerobic Threshold by Gas-Exchange. J Appl Physiol 60: 2020-2027, 1986), and it has been clarified that it corresponds to an intensity of about 50 to 70% of the maximum oxygen uptake of an individual. At the site of current exercise therapy, the maximum oxygen uptake is used as an index of endurance, but if measurement is difficult, a ventilatory work threshold value is often used.

Exercise therapy for hippocampal neurogenesis in the present invention is preferably low intensity exercise therapy. VT is commonly used well in the clinic as an international indicator of exercise intensity according to human physical strength level. The low intensity exercise therapy in the present invention refers to therapy with exercise of intensity of V T or less (Mateika J H, Duffin J. Ventilatory responses to exercise performed below and above the first ventilatory threshold. Eur J Appl Physiol Occup Physiol 68: 327-335, 1994). Since VT can be measured without requiring maximum effort, it can be used for elderly people, diseased persons, or animal experiments, etc.

As a model of the low intensity exercise therapy in humans, in the case of a bicycle ergometer, there may be mentioned exercise once for 40 to 50 minutes with 35% intensity of maximal oxygen uptake.

The composition of the present invention preferably regenerates hippocampal nerve by up regulation of genes which comprises at least one gene selected from the group consisting of Igflr (insulin-like growth factor 1 receptor), Lep (leptin) and Cxcr4 (chemokine C—X—C motif receptor 4).

The composition of the present invention may be a medicine or a food.

As the medicine, it may be formulated into a capsule, a solution, a suspension, an emulsion, a syrup, an elixir, an injection, a suppository, an inhalant, a transnasal, a transdermal agent, etc., according to the conventional manner, but it is not limited to these.

As the food, it may be formulated into a supplement, a solid food, a fluid food, a beverage, etc., according to the conventional manner, but it is not limited to these.

EXAMPLES

Next, the present invention will be explained in more detail with reference to Examples, but the present invention is not limited to the following Examples unless it goes beyond its gist.

The present inventors investigated the single effect of ASX which enhances hippocampal function and estimated its molecular mechanism. Further, in order to investigate whether or not the effect of improving hippocampal function by low intensity exercise is enhanced by ASX ingestion, a low intensity exercise model based on a ventilatory work threshold value (VT, ventilatory threshold) in mouse was firstly established, and investigated the effect of the combination of the low intensity exercise of VT or less and ASX uptake on AHN and spatial cognitive function of hippocampus, and the molecular mechanism thereof was estimated.

A. Establishment of Low Intensity Exercise Model Based on Ventilatory Work Threshold Value 1. Object In order to establish a running exercise model based on VT, a metabolic chamber treadmill for small animal was used, VT at running exercise of mouse was measured and an object was to set low intensity exercise intensity of VT or less.

2. Method 2-1. Test Animals and Breeding Conditions

This experiment was carried out with the approval of the Animal Experiment Committee based on the Animal Experimental Guidelines of the University of Tsukuba. In experiment animals, 11 week old C57BL/6J male mice (26 to 28 g, SLC, Japan) were used. The breeding environment was constantly maintained at indoor temperature of 22±2° C. and indoor humidity of 60±10% at all times. For the feed, solid feed for experimental animals (MF, Oriental Yeast Industry, Japan) was used, and for drinking water distilled water was used, and free access was taken for both for 24 hours. The lighting was taken as a light/dark cycle bordering between 7:00 am and 7:00 pm. Weight was measured daily for weight control of the mouse.

2-2. Running Learning

Running learning using a chamber treadmill for the mouse was carried out for 10 days after preliminary breeding of the mouse. Running learning was carried out seven times in total with 30 minutes per a day, and a frequency of 5 times a week. The exercise speed of the running learning was gradually increased from 5 m/min to 25 m/min during seven times of enforcement. The protocol of the running learning is shown in Table 1.

TABLE 1

Protocol of running learning

| | |
|---|---|
| $1^{st}$ day | 5 m per min (5 min) + 10 m per min (15 min) |
| $2^{nd}$ day | 10 m per min (10 min) + 12.5 m per min (20 min) |

TABLE 1-continued

Protocol of running learning

| | | |
|---|---|---|
| $3^{rd}$ day | Rest | |
| $4^{th}$ day | 10 m per min (10 min) + 12.5 m per min (10 min) + 15 m per min (10 min) | |
| $5^{th}$ day | 12.5 m per min (10 min) + 15 m per min (10 min) + 17.5 m per min (10 min) | |
| $6^{th}$ day | Rest | |
| $7^{th}$ day | 15 m per min (10 min) + 17.5 m per min (10 min) + 20 m per min (10 min) | |
| $8^{th}$ day | 17.5 m per min (10 min) + 20 m per min (10 min) + 22.5 m per min (10 min) | |
| $9^{th}$ day | Rest | |
| $10^{th}$ day | 20 m per min (10 min) + 22.5 m per min (10 min) + 25 m per mim (10 min) | |
| $11^{st}$ day | Rest | |
| $12^{nd}$ day | Rest | |
| $13^{rd}$ day | Gradually increasing load running actual test | Fixed load running exercise test |

2-3. Gradually Increasing Load Running Test

After entering the metabolic chamber, the mouse was rested for one hour until it was stabilized at the normal value of exhalation gas (50 ml/kg/min or less) (Schefer and Talan, 1996). After the exhalation gas stabilized, the running test was carried out with an exercise manner by starting with a speed of 3 m per minute, and gradually increasing the speed of 2.5 m/min every 3 minutes, and finished the running test when the mouse could not keep the pace (FIG. 1). This running exercise was gradually increased until the mouse exhausted.

During the gradually increasing load running, exhalation gas was measured every after one minute. For the measurement, a metabolic chamber treadmill and Oxymax equal flow system (Columbus Instrument, Columbus, Ohio) were used. Calibration was carried out by a mixed gas (20.98% $O_2$, 0.48% $CO_2$), and the gas in the chamber was compulsorily replaced with an air flow amount set in advance. Thereafter, based on the set air flow amount, from the standard value of the injected gas and variation of the discharged gas concentration in the chamber, $VO_2$ (oxygen uptake), $VCO_2$ (carbon dioxide discharge amount), and exhalation gas exchange ratio (RER=respiratory exchange ratio) were calculated. For calculation of VT, referring to the V-slope method by Beaver et al. (1986), the value of $VO_2$ vs $VCO_2$ excluding the data at the beginning of exercise and during vigorous exercise from the obtained exhalation gas data ($VO_2$, $VCO_2$) was subjected to linear regression by the least square method and the intersection point was made VT.

2-4. Fixed Load Running Exercise Test

In order to investigate the validity of the different exercise intensity with reference to VT, a fixed load running exercise test was carried out. Two days after the running learning, by using the rest group (SED, n=7), exercise load of (sub-VT, n=7) in which an intensity is VT or less and (supra-VT, n=7) in which an intensity is VT or more, a fixed load running exercise test for 30 minutes were carried out. After mice were rested on a treadmill for 15 minutes, running exercise was started, and immediately after completion of running exercise for 30 minutes, the rest group and running exercise were extinguished, and the bloods were collected (FIG. 1). The bloods collected were subjected to heparin treatment, and then, lactic acid levels and blood glucose levels in the bloods were measured by using a glucose/lactate analyzer (2300 Stat Plus, YSI, USA).

2-5. Statistical Processing

All data were expressed as an average value±standard error of each sample. For the statistical processing of lactic acid level and blood glucose level, after one-way analysis of variance (One-way ANOVA), Bonferroni's tests method was used as a post-hoc test. All the significance levels were set to less than 5%.

3. Results 3-1. Dynamics of Exhalation Gas Parameters

Figure 2:
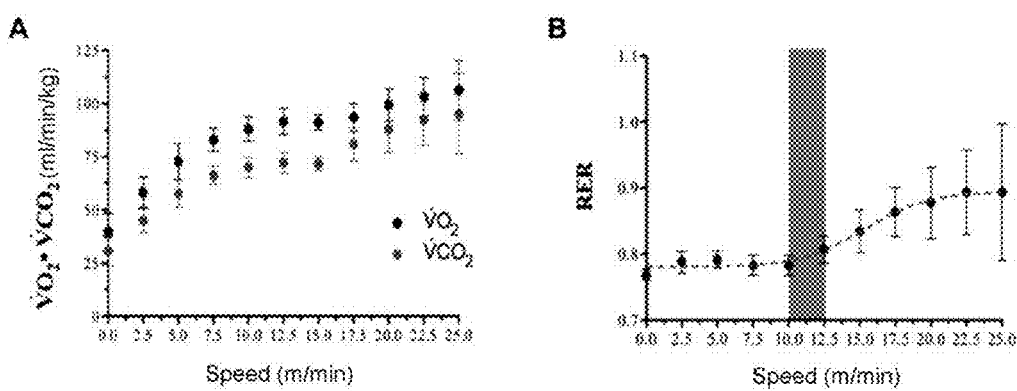
FIG. 2 shows $VO_2$, $VCO_2$ and RER in the gradually increasing load exercise by the treadmill in Example.

The changes with time of $VO_2$, $VCO_2$ and RER during the gradually increasing load running exercise are shown in FIG. 2. All the measurement items increased in intensity dependently. RER abruptly increased between 10 m/min and 12.5 m/min.

3-2. Evaluation of Ventilatory Work Threshold Value

Figure 3:
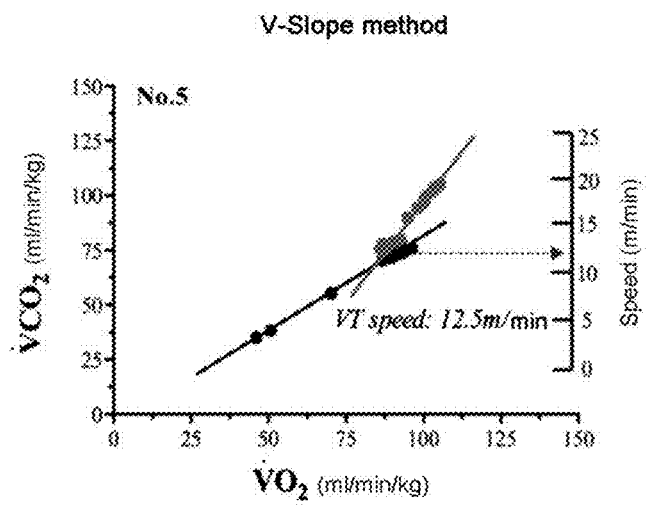
FIG. 3 shows the VT measurement by the V-slope method in Example.

VT was calculated by the V-slope method using $VO_2$ and $VCO_2$ obtained during the gradually increasing load exercise (FIG. 3). The VT of this individual was 12.5 m/min. Based on the V-slope method, the VT of each individual and the RER at that time are shown in Table 2.

TABLE 2

Treadmill speed with VT and RER with VT

| Animal | Speed (m/min) with VT | RER with VT |
|---|---|---|
| 1 | 10 | 0.79 |
| 2 | 12.5 | 0.81 |
| 3 | 15 | 0.84 |
| 4 | 12.5 | 0.84 |
| 5 | 12.5 | 0.82 |
| 6 | 12.5 | 0.85 |
| 7 | 10 | 0.77 |
| Average | 12.1 | 0.82 |
| SEM | 1.7 | 0.06 |

As a result of calculating the average of each individual, the average VT during gradually increasing load running used in this study was 12.1 m/min, and the average value of RER at that time was 0.82. It was the intensity of VT or less.

3-3. Validity of Exercise Different in VT Standard

Figure 4:
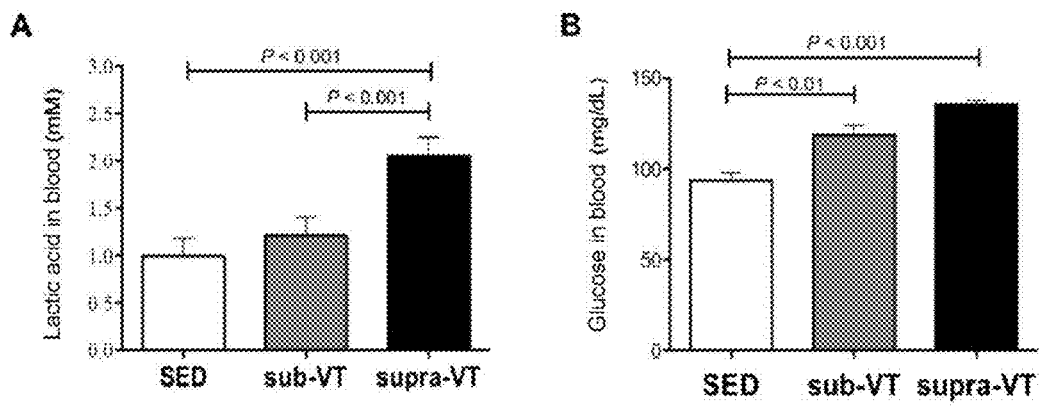
FIG. 4 shows the response of the blood parameters after acute exercise by the treadmill in Example.

Lactic acid levels in blood and blood glucose level were measured immediately after fixed load running exercise with a transient VT or less (7 m/min) and VT or more (17 m/min) based on VT (FIG. 1). The lactic acid levels of the exercise group of VT or more were significantly increased as compared with those of the rest group and the exercise group of VT or less. Further, in the exercise group of VT or more and the exercise group of VT or less, the blood glucose levels were significantly increased as compared with those of the rest group (FIG. 4).

4. Consideration

Here, in order to establish the intensity of low intensity exercise in a healthy mouse, which is an experimental animal in this study, focusing on non-invasively measurable VT, the VT was measured using a metabolic chamber treadmill for small animals to confirm the validity of the low intensity exercise of VT or less.

As a result, the VT of the mouse appeared at a running speed of 12.1±1.7 m per minute, and the RER at the VT was 0.82 (FIG. 2). Until now, since the RER of human at the time of VT was about 0.85 to 0.9, the VT of the mouse clarified in this study was correctly measured and it showed that the reliability was sufficient. Subsequently, in order to confirm the validity of exercise intensity based on this VT, as reported by Soya, et al. (Soya H, Mukai A, Deocaris C C, Ohiwa N, Chang H, Nishijima T, Fujikawa T, Togashi K, Sai to T. Threshold-like pattern of neuronal activation in the hypothalamus during treadmill running: establishment of a minimum running stress (MRS) rat model. Neurosci Res 58: 341-348, 2007), it was studied from the change in lactic acid in blood by the different transient exercise based on the VT. Immediately after imposing transient low intensity (7 m/min) and high intensity (17 m/min) based on the VT, in the low intensity exercise, lactic acid in blood was not increased and increase was observed only in the high intensity exercise (FIG. 4).

Accordingly, the validity of the running exercise model based on the VT of the mouse was confirmed. Further, it is assumed that similar to the improvement of AHN and spatial cognitive function, in the low intensity exercise based on LT in rats, the low intensity exercise of VT or less set in this study promotes AHN and improves spatial cognitive function.

5. Summary

Here, by using healthy mice, a low intensity model based on the VT which is a non-invasive exercise index was established. As a result, the following findings were obtained.

1) The speed at the time of the VT of the mouse was set at 12.1 m/min, the speed of the VT or less was 7 m/min, and the speed of the VT or more was 17 m/min.

2) It was recognized that the lactic acid level in blood was significantly elevated in the exercise group of the VT or more as compared with those of the rest group and the exercise group of the VT or less.

3) It was recognized that the blood glucose level was significantly elevated in the exercise group of the VT or more and the exercise group of the VT or less as compared with those of the rest group.

From the above, VT, which is one of exercise intensity index, was clarified using mice, and a low intensity exercise model of the VT or less was established (7 m/min).

B. Influence of Combined Use of Low Intensity Exercise and ASX Uptake on AHN and Spatial Cognitive Function 1. Object For the purpose of clarifying whether or not hippocampal function improving effect is enhanced by low intensity exercise, influence of combined use of low intensity exercise (7 m/min) of VT or less and ASX uptake (0.5% by weight) on AHN and spatial cognitive function was investigated.

2. Method 2-1. Test Animals and Breeding Conditions

It was the same as above.

2-2. Grouping

Figure 5:
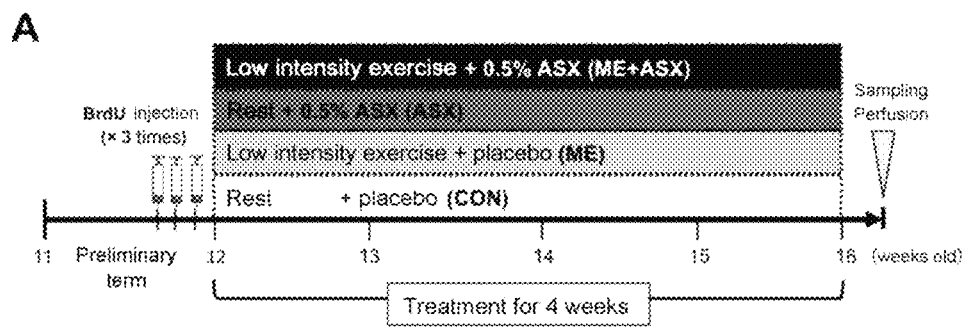
FIG. 5 shows experimental design in Example.
Figure 5:
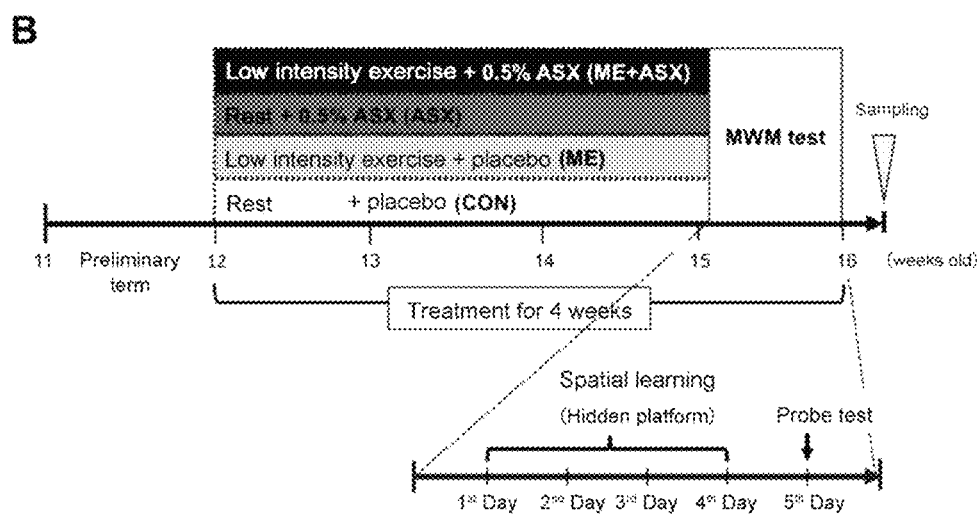

All the mice used in this experiment were divided so that the weight was equalized at the preliminary breeding end point. These were divided into four groups of placebo+rest (CON), placebo+low intensity exercise (ME), 0.5% ASX uptake+rest (ASX), and the low intensity exercise+0.5% ASX uptake (ME+ASX) (FIG. 5). Mice were bred each one per a cage.

2-3. Intake of ASX Mixed Diet or Placebo 0.5% ASX uptake or placebo uptake was carried out.

2-4. Training of Low Intensity Exercise

The protocol of running exercise training is shown in Table 3.

TABLE 3

| Protocol of low intensity exercise | |
| --- | --- |
| 1st day | 3 m/min (10 min) + 5 m/min (20 min) |
| 2nd day | 5 m/min (30 min) |
| 3rd day | Rest |
| 4th day | 5 m/min (20 mm) + 7 m/min (10 min) |
| 5th day | 5 m/min (10 mm) + 7 m/min (20 mm) |
| 6th day | 7 m/min (30 min) |
| 7th day | Rest |

TABLE 3-continued

| Protocol of low intensity exercise | |
| --- | --- |
| 8th day | 7 m/min (30 min) |
| 9th day | 7 m/min (30 min) |
| 10th day | Rest |
| 11st day | 7 m/min (30 min) |
| 12nd day | 7 m/min (30 min) |
| 13rd day | 7 m/min (30 min) |
| 14th day | Rest |
| 15th day | 7 m/min (30 min) |
| 16th day | 7 m/min (30 min) |
| 17th day | Rest |
| 18th day | 7 m/min (30 min) |
| 19th day | 7 m/min (30 min) |
| 20th day | 7 m/min (30 min) |
| 21st day | Rest |
| 22nd day | 7 m/min (30 min) |
| 23rd day | 7 m/min (30 min) |
| 24th day | Rest |
| 25th day | 7 m/min (30 min) |
| 26th day | 7 m/min (30 min) |
| 27th day | 7 m/min (30 min) |
| 28th day | Rest |

The mice in the low intensity exercise group imposed a treadmill running exercise of 7 m/min for 30 minutes a day. Also, the mice in the rest group were placed on the treadmill for equal time with the running exercise training and were not allowed to exercise anything (control experiment). For the running exercise training, a treadmill for small animals (KN-73, Natsume, Japan) was used. In either of the groups, training or control experiment was imposed once a day in the dark period, which became active for mice.

2-5. Administration of Neoplastic Cell Marker BrdU

BrdU (bromodeoxyuridine) is taken up as an analog molecule of thymidine into the cell nucleus at the S phase of the cell cycle and is used to evaluate cell division, proliferation, and subsequent survival. Thus, BrdU (100 mg/kg BW) was intraperitoneally administered to all mice during three days before starting running exercise and 0.5% ASX uptake (FIG. 5). Administration was carried out only once a day (AM8:00).

2-6. Bio Reflux Fixation

Living perfusion fixation was carried out.

2-7. Preparation of Brain Tissue Section

Preparation of brain tissue sections was carried out.

2-8. Calculation of Hippocampal Dentate Gyrus Volume

The hippocampal dentate gyrus volume was calculated.

2-9. Evaluation of Neoplastic Cell and their Maturation Stage

Immunohistochemical staining method is a method of labeling and visualizing a target DNA or protein on a tissue utilizing an antigen antibody reaction. In visualization, it is carried out by labelling an enzyme or a fluorescent substance, etc., which is a substance to be a marker, to an antibody which bounds to an antigen, and reacting with the marker to colorize the antibody adhered portion. In this experiment, fluorescent antibody method was used for evaluation of proliferating cells, viable cells and newly matured neurons.

[BrdU/NeuN]

In this experiment, BrdU was identified for the evaluation of neoplastic cells. For identification, rat anti-BrdU antibody (Rat anti-BrdU, AbD Serotec) was used as a primary antibody and CyTM3 donkey anti-rat IgG antibody (Cy3 Donkey Anti-Rat IgG, JACKSON) was used as a secondary antibody to fluorescently label with red color and visualized. In addition, for identification of mature neurons, mouse anti-NeuN antibody (Mouse Anti-Neuronal Nuclei monoclonal antibody, Chemicon) was used as a primary antibody, and for visualization, a fluorescently labeled secondary antibody AMCA donkey anti-mouse IgG antibody (AMCA Donkey Anti-Mouse IgG, JACKSON) was used and stained to blue color.

According to this procedure, newly matured cells were evaluated by BrdU+/NeuN+ reaction (red+bluish white). The procedures of the fluorescent antibody method were shown below.

A) Primary Antibody Reaction
1) Wash with PB (0.1 M phosphate buffer). 5 min×2 times
2) Wash with PB-T (1% Triton-X and 1% BSA in 0.1 M phosphate buffer). 5 min×3 times
3) Cleavage of DNA double strand: React with 2M HCl at 37° C. for 30 minutes.
4) Wash with PB-T. 10 min×3 times
5) Removal of nonspecific binding (blocking): 2% NDS/PB-T (2% normal donkey serum in PB-T) is allowed to react at room temperature for 30 minutes.
6) Dilute the primary antibody with 2% NDS/PB-T (dilution rate; anti-BrdU antibody: 500-fold, anti-NeuN antibody: 500-fold), incubate at room temperature for 2 hours and react at 4° C. for 48 hours.
B) Visualization (Fluorescent Method)
7) Wash with PB-T. 10 min×3 times
8) Dilute the fluorescently labeled secondary antibody with 2% NDS/PB-T (dilution rate; Cy3: 500-fold, AMCA: 500-fold), and react at 4° C. for 24 hours. Incidentally, it shielded from light during the reaction.
9) Wash with PB-T. 10 min×2 times
10) Wash with PB. 5 min×2 times
11) Paste on the slide glass and seal it.

[Ki67/NeuN]

In this experiment, for evaluation of cell proliferation, it was identified by Ki67. For identification, rabbit anti-Ki67 antibody (Rabbit anti-Ki67, Abcam) was used as a primary antibody, and Alexa 555 anti-rabbit IgG antibody (Goat Alexa 555 anti-rabbit IgG, Biotium) was used as a secondary antibody to fluorescently label with red color and visualized. In addition, for identification of the matured neurons, mouse anti-NeuN antibody (Mouse Anti-Neuronal Nuclei monoclonal antibody, Chemicon) was used as a primary antibody, and for visualization, a fluorescently labeled secondary antibody AMCA donkey anti-mouse IgG antibody (AMCA Donkey Anti-Mouse IgG, JACKSON) was used and stained to blue color. According to this procedure, newly matured cells were evaluated by Ki67+/NeuN+reaction (red+bluish white). The procedures of the fluorescent antibody method were shown below.

A) Primary Antibody Reaction
1) Wash with PB (0.1 M phosphate buffer). 5 min×2 times
2) Wash with PB-T (1% Triton-X and 1% BSA in 0.1 M phosphate buffer). 5 min×3 times
3) Wash with PB-T. 10 min×3 times
4) Removal of nonspecific binding (blocking): 2% NDS/PB-T (2% normal donkey serum in PB-T) is allowed to react at room temperature for 30 minutes.
5) Dilute the primary antibody with 2% NDS/PB-T (dilution rate; anti-Ki67 antibody: 500-fold, anti-NeuN antibody: 500-fold), incubate at room temperature for 2 hours and react at 4° C. for 48 hours.
B) Visualization (Fluorescent Method)
12) Wash with PB-T. 10 min×3 times
13) Dilute the fluorescently labeled secondary antibody with 2% NDS/PB-T (dilution rate; Alexa 555: 250-fold, AMCA: 250-fold), and react at 4° C. for 24 hours. Incidentally, it shielded from light during the reaction.
14) Wash with PB-T. 10 min×2 times
15) Wash with PB. 5 min×2 times
16) Paste on the slide glass and seal it.

2-10. Estimation Method of Cell Number

An estimation method of cell number was carried out.

2-11. Evaluation of Spatial Learning Memory Ability: Morris Water Maze (MWM)

Evaluation of spatial learning memory ability was carried out.

2-12. Statistical Processing

All data were expressed as an average value±standard error of each sample. For the statistical processing of neurons, a two-way factorial analysis of variance (Two-way ANOVA) was used, and Bonferroni's post-hoc was carried out, if necessary. All the significance levels were set to less than 5%.

3. Results 3-1. Change in Number of Neoplastic Cells

Figure 6:
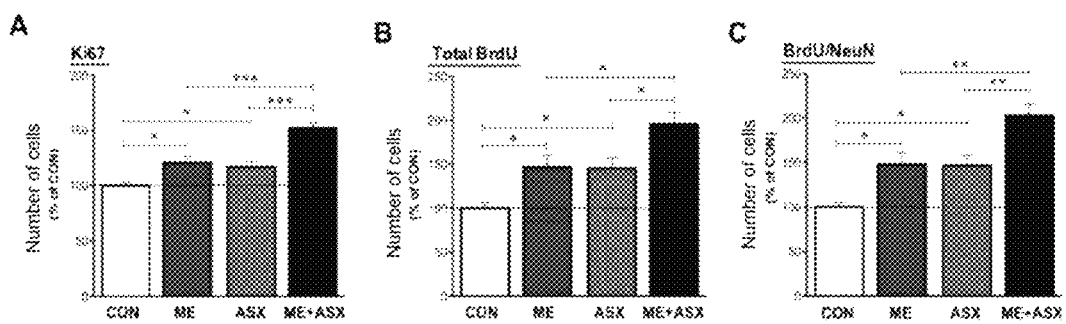
FIG. 6 shows the effect of low intensity exercise and astaxanthin uptake on adult hippocampal neurogenesis in Example.

The influence of the low intensity exercise and ASX uptake on the neurogenesis of the hippocampus is shown in FIG. 6. The number of Ki67 positive cells, which are a cell proliferation marker, was found to have the main effect of exercise ($F_{(1, 26)}=34.20$, $P<0.001$) and the main effect of ASX ($F_{(1, 26)}=25.90$, $P<0.001$). Further, as a result of Bonferroni's post-hoc test, a significant increase was observed in the ME group and the ASX group as compared with the CON group ($P<0.05$), and a significant increase was observed in the ME+ASX group as compared with the ME group and the ASX group ($P<0.001$). The number of BrdU positive cells was found to be the main effect of exercise ($F_{(1, 24)}=17.20$, $P<0.001$) and the main effect of ASX ($F_{(1, 24)}=16.05$, $P<0.001$). Moreover, as a result of Bonferroni's post-hoc test, a significant increase was observed in the ME group and the ASX group as compared with the CON group ($P<0.05$), and a significant increase was observed in the ME+ASX group as compared with the ME group and the ASX group ($P<0.05$). The number of BrdU/NeuN positive cells was found to be the main effect of exercise ($F_{(1, 24)}=19.50$, $P<0.001$) and the main effect of ASX ($F_{(1, 24)}=18.39$, $P<0.001$). As a result of Bonferroni's pos-hoc test, a significant increase was observed in the ME group and the ASX group as compared with the CON group ($P<0.05$), and a significant increase was observed in the ME group and the ASX group as compared with the CON group ($P<0.01$). On the other hand, in the result of AHN, no interaction of exercise×ASX was observed.

3-2. Result of MWM: Spatial Learning Escape Training

Figure 7:
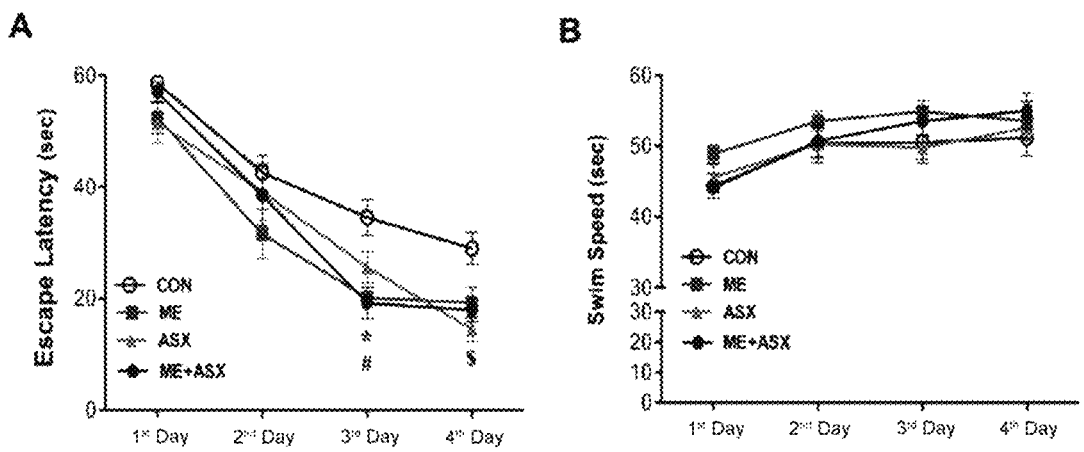
FIG. 7 shows the effect on low intensity exercise and astaxanthin's spatial learning in Example.

The escape time during place learning escape training is shown in FIG. 7. The swimming time was found to be the main effect of Day ($F_{(3, 33)}=109.50$, $P<0.0001$) and the main effect of Group ($F_{(3, 33)}=5.70$, $P<0.01$). A significant shortening of the escape time was observed for each group by repeatedly learning. Further, as a result of the post-hoc test, a significant shortening was observed on the third day in the ME group and the ME+ASX group as compared with the CON ($P<0.05$). A significant shortening was observed on the ASX group on the fourth day ($P<0.05$). There was no significant difference in swimming speed among the groups (FIG. 7A).

3-3. Result of MWM: Probe Test

Figure 8:
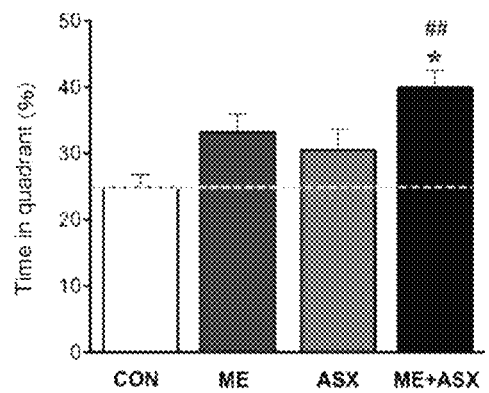
FIG. 8 shows the effect of low intensity exercise and astaxanthin on the spatial memory in Example.

In each group, the ratio of the cumulative time of swimming within the quadrant where the platform existed to the total swimming time is shown in FIG. 8. The ratio of the cumulative time was found to be the main effect of exercise ($F_{(1, 34)}=11.49$, $P<0.01$) and the main effect of the ASX ($F_{(1, 34)}=5.55$, $P<0.05$). As a result of post-hoc test, in the ME+ASX group (39.9%), elongation of the total swimming time was confirmed as compared with the ASX group (30.5%) ($P<0.05$). Further, as a result of Bonferroni's multiple comparison test, the ratio of the cumulative time in the ME+ASX group was significantly higher than that of the CON group (24.8%) ($P<0.01$).

4. Consideration

Here, in order to clarify whether or not improvement of the hippocampal function due to the low intensity exercise is enhanced by ASX uptake, influence of combined use of the low intensity exercise of VT or less and 0.5% ASX uptake on AHN and spatial learning memory ability was investigated. For the evaluation of AHN, the numbers of proliferating cells (Ki67+), viable cells (BrdU+), and newly matured cells (BrdU+/NeuN+) were counted using immunohistochemical staining method and the result thereof was shown by the rate of change relative to the CON group. Also, the spatial learning memory ability was evaluated using the MWM with regard to acquiring ability (learning) of memory by the place learning escape training for 4 days, and retention and recollection ability of memory by the probe test on the fifth day.

As compared with the CON group, the number of proliferating cells (+20.5%), the number of viable cells (+46.6%), and the number of newly matured cells (+47.8%) are significantly increased in the ME group, and at this time, it was confirmed that the result of acquiring ability (learning) of memory and retention and recollection ability of memory were significantly improved. Similar to the prior research carried out using the low intensity exercise of LT or less (Inoue K, Hanaoka Y, Nishijima T, Okamoto M, Chang H, Saito T, Soya H. Long-term mild exercise training enhances hippocampus-dependent memory in rats. Int J Sports Med 36: 280-285, 2015; Inoue K, Okamoto M, Shibato J, Lee M C, Matsui T, Rakwal R, Soya H. Long-term mild, rather than intense, exercise enhances adult hippocampal neurogenesis and greatly changes the transcriptomic profile of the hippocampus. PLoS One 10: e0133089, 2015), it has been shown that the low intensity exercise of VT or less also improves AHN and hippocampal function, so that it can be said that the low intensity exercise carried out in this research was reasonable. In addition, it was confirmed that the number of proliferating cells (+16.9%), the number of viable cells (+44.9%), and the number of newly matured cells (+46.3%) increased significantly in the ASX group and the result of the MWM was significantly improved. Accordingly, reproducibility of enhancing AHN and hippocampal function by the ASX uptake of 0.5% was confirmed.

ME+ASX significantly increased the number of proliferating cells (+52.3%), the number of viable cells (+95.7%), and the number of newly matured cells (+102.9%) as compared with the CON group. Further, it was clarified that the combined use of the low intensity exercise and ASX uptake exceeds the combined effect of each single group (ME group, ASX group). In addition, with respect to the effect of improving the spatial memory capacity, the increase rate for the CON group was confirmed to be 33.5% increase in the ME group and 25.9% in the ASX group, and further 60.6% in the ME+ASX group, which were the same results as in the AHN. In the prior research, the combined use of antioxidant substances and rich behavior (exercise, learning) shows a synergistic effect over the sum of individual effects on reduction of amyloid β which is one of causes of Alzheimer's disease (Pop V, Head E, Hill M A, Gillen D, Berchtold N C, Muggenburg B A, Milgram N W, Murphy M P, Cotman C W. Synergistic effects of long-term antioxidant diet and behavioral enrichment on beta-amyloid load and non-amyloidogenic processing in aged canines. J Neurosci 30: 9831-9839, 2010). In this research, the improvement effect of AHN and memory capacity by the ME+ASX group also exceeded the sum of each independent group (ME group, ASX group), so that it was clarified for the first time that the combination of the low intensity exercise and ASX uptake synergistically increases AHN and hippocampal function.

5. Summary

Here, influence of combined use of the low intensity exercise of VT or less and ASX uptake on AHN and spatial cognitive function was investigated, and the following results were obtained.

1) Promotion of AHN (proliferating cells, viable cells, and neonatal mature neurons) by the low intensity exercise and ASX uptake alone was confirmed.

2) AHN promoting effect by the low intensity exercise was enhanced by combined use of the ASX uptake, resulting in a synergistic effect.

3) Acquisition of memories by learning of low intensity exercise and ASX uptake alone (learning) and improvement of task performance in retention and recollection of memory were recognized (main effect).

4) Improvement in retention and recollection of memory by the low intensity exercise was enhanced by ASX uptake, resulting in a synergistic effect.

From the above results, it became clear for the first time that ASX uptake (0.5%) not only enhances the hippocampal function alone but also enhances the hippocampal function improving effect by the low intensity exercise and brings about a synergistic effect.

C. Investigation of Molecular Mechanism of Hippocampal Function Improvement by Combined Use of Low Intensity Exercise and ASX Uptake 1. Object Changes in hippocampal gene expression were comprehensively studied by using the microarray method. Based on the expression of all genes identified in microarrays, using IPA analysis which is a state-of-the-art functional analysis method, it is an object to estimate the molecular mechanism which synergistically enhancing AHN and memory ability by combined use of the low intensity exercise and ASX uptake.

2. Method 2-1. Test Animals and Breeding Conditions

Experiments were carried out with the same experimental animals as above and breeding conditions.

2-2. Grouping

All the mice used in this experiment were divided so that the weight was equalized at the preliminary breeding end point. These were divided into three groups of placebo+rest (CON), placebo+low intensity exercise (ME), and low intensity exercise+0.5% ASX uptake (ME+ASX) (each n=8). Mice were bred each one per a cage.

2-3. Extraction of Hippocampus

The brain was removed two days after 4 weeks training and ASX uptake. The hippocampus was fractionated from the collected brain (Hirano M, Rakwal R, Shibato J, Sawa H, Nagashima K, Ogawa Y, Yoshida Y, Iwahashi H, Niki E, Masuo Y. Proteomics- and transcriptomics-based screening of differentially expressed proteins and genes in brain of Wig rat: a model for attention deficit hyperactivity disorder (ADHD) research. J Proteome Res 7: 2471-2489, 2008). The hippocampus was immediately frozen with liquid nitrogen and stored in a freezer at −80° C.

2-4. Homogenization

The hippocampi were crushed and stored in 2 ml test tube.

2-5 Extraction of Hippocampal RNA

Hippocampal RNA extraction was carried out.

2-6. Measurement of RNA Concentration and Property Confirmation

The concentration and quality of the extracted RNA was confirmed.

2-7. Comprehensive Analysis of Hippocampal Gene Expression: Microarray

In this experiment, SurePrint G3 mouse 8×60K whole genome DNA microarray chip (G4858A, Agilent Technologies, Palo Alto, Calif., USA) was used for RNA analysis. In the following, the procedure is shown.

1) Mixing of RNA: RNA extracted from hippocampus samples of each individual (n=8, 250 ng/1 individual) was mixed for each group.

2) Labeling of RNA: RNA extracted from each sample is labeled with Cy3 and Cy5 dyes (Two-color labeling) using an Agilent Low RNA Input Fluorescent Linear Amplification Kit (Agilent Technologies).

3) Hybridization: Samples of fluorescently labeled control group (CON group) and experiment group (ME group, ME+ASX group) are assayed on the same Microarray chip and hybridized with a 60 base pair probe on the slide glass. Conditions for hybridization and washing were in accordance with the conditions of the manufacturer.

4) Scan: Hybridized Microarray chip was scanned with Agilent Microarray scanner G2505C.

5) Processing of scan data: In order to clarify the change in gene expression in the experiment group using the control group as a control, slide images were processed using Agilent Feature Extraction software. In the program at this time, the color intensity of Cy3 and Cy5 of all the probes was measured.

6) Standardization of data: For standardization of data, LOWESS (locally weighted linear regression) was used, and logarithmic and logarithmic error rates standardized from Cy3 and Cy5 signals were calculated. The level of significance at this time was set at 1%.

7) Data acquisition: A list of genes that came out up to 6) was prepared using GeneSpring version GX 10 (Agilent). The gene list was created by extracting only genes whose gene expression was enhanced by 1.5-fold or more and genes suppressed to 0.75-fold or less with both intensities using the control group as a control. At this stage, the increase and decrease in gene expression and its strength are shown in the Table.

2-8. IPA Analysis

IPA (Ingenuity Pathways Analysis, www.ingenuity.com) is software that can interpret biological functions and analyze networks based on data obtained from microarray experiments. The data on gene expression whose changes were observed in ME and ME+ASX were input into IPA. In particular, IPA analysis at this time is limited to hippocampal gene expression, and a large amount of gene expression was classified by physiological function by Ingenuity Knowledge Base developed based on past thesis. In addition, networks between each gene were predicted and ranked in network order which seems to be important for statistical (P<0.05, right-tailed Fisher's exact test). Here, focusing on genes reported to be related to AHN and spatial learning memory in past articles from among networks constructed by IPA analysis, it was decided to estimate the molecular mechanism which results in hippocampal adaptation by the combined use of the low intensity exercise and ASX uptake.

2-9. RT-PCR

In order to confirm the reproducibility and validity of the molecular mechanism estimated by the microarray and IPA analysis, 12 genes were picked up and the changes in their gene expression were reexamined by RT-PCR.

2-10. Statistical Processing

All data were expressed as an average value±standard error. For statistical processing of RT-PCR, after one-way analysis of variance (One-way ANOVA), the Bonferroni's tests method was used as post-hoc. All the significance levels were set to less than 5%.

3. Results 3-1. Measurement of RNA Concentration and Presence or Absence of Contamination The OD ratios (A260:280, A260:230) of each individual and the results of electrophoresis of total RNA were obtained. The OD ratio of A260:280 and A260:230 was 1.8 or more of the reference value for all individuals. For all individuals, ribosomal RNA bands of 18 S and 28 S were confirmed.

3-2. Changes in Hippocampal Gene Expression: Microarray and IPA

Changes in the number of genes that were enhanced by 1.5-fold or more, or genes that were suppressed to 0.75-fold or less as compared with the CON group in the microarray were obtained. Of the 55,681 genes arranged on the chip of the microarray, the number of genes whose expression was enhanced in ME was 2,209 and the number of suppressed genes was 564. On the other hand, the gene enhanced by ME+ASX was 3,891, and the gene which was suppressed was 411. As a result of focusing the hippocampal gene alone, and inputting the gene change obtained in the microarray into IPA, the gene whose expression was enhanced only by ME was 123, and the gene which was suppressed was 32. The gene whose expression was enhanced only by ME+ASX was 108, and the gene which was suppressed was 14. The gene whose expression was enhanced by both groups was 134, and the gene which was suppressed was 3.

3-3. Network Analysis: IPA

Figure 9:
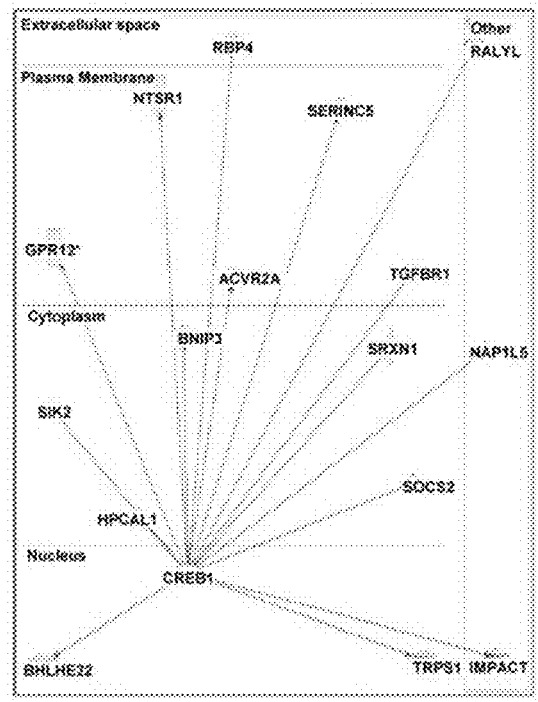
FIG. 9 shows top two gene networks responding to low intensity exercise in Example.
Figure 9:
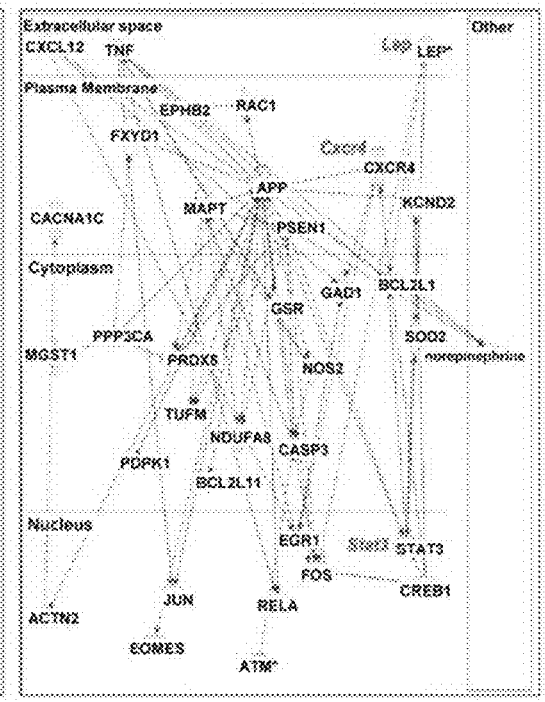
Figure 10:
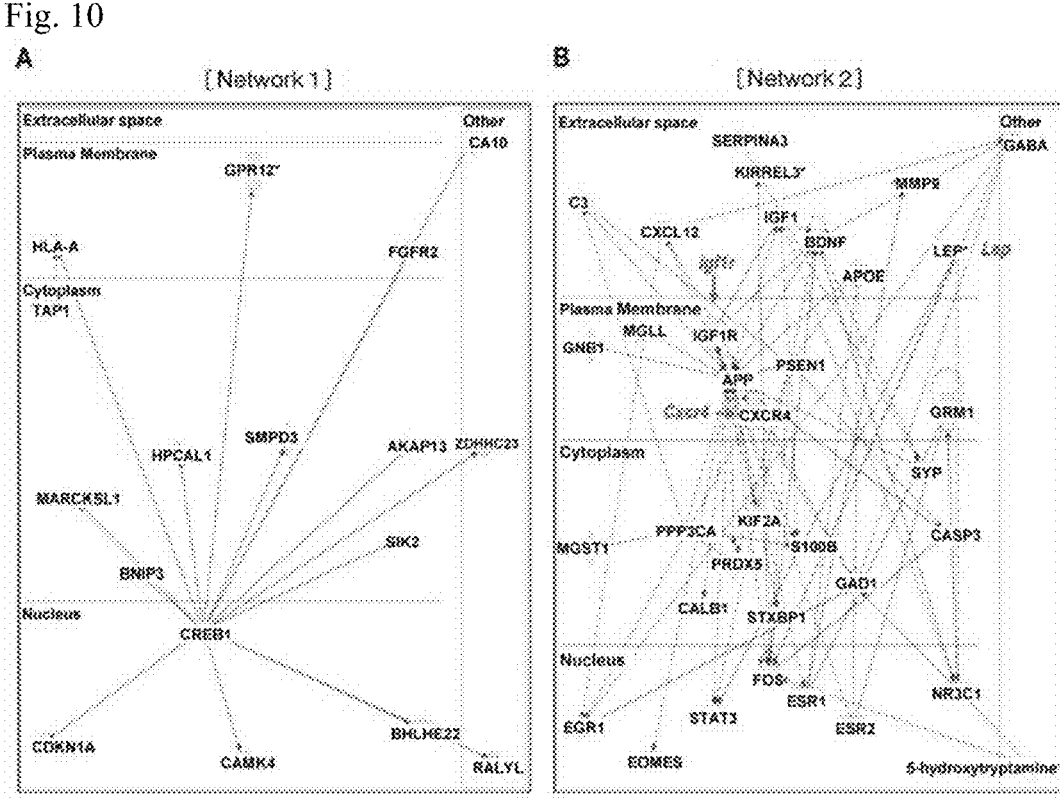
FIG. 10 shows the top two gene networks responding to low intensity exercise plus astaxanthin in Example.

The results of network analysis by IPA analysis were shown in FIGS. 9 (ME) and 10 (ME+ASX). In the ME group, enhancement of Lep (leptin), Cxcr4 (chemokine receptor 4) and Stat3 (Signal transducer and activator of transcription 3) genes were shown (FIG. 9B). In the ME+ASX group, enhancement of Lep and Cxcr4 genes have been shown similar to the ME group, and it was estimated to enhance Igflr (insulin-like growth factor 1 receptor) gene expression (FIG. 10B).

3-4. Investigation of Gene Expression by RT-PCR

Figure 11:
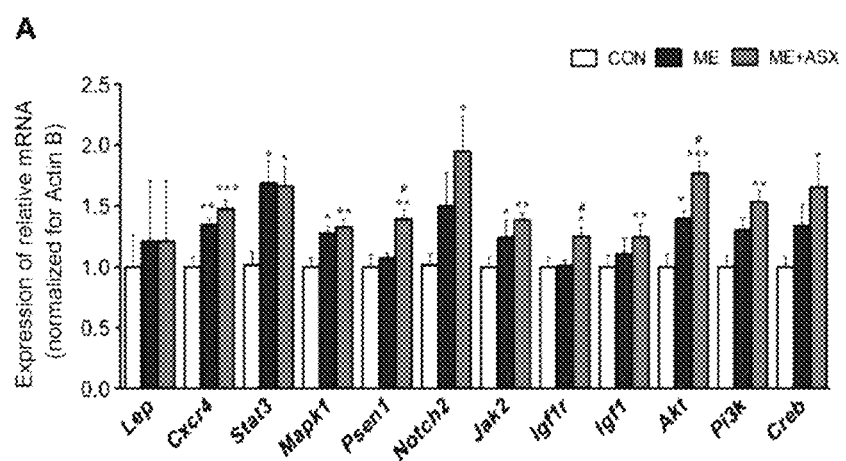
FIG. 11 shows confirmation of gene expression by RT-PCR in Example.

From the results of DNA microarray and IPA network analysis, as for the noticed gene, mRNA expression was confirmed using RT-PCR (FIG. 11). As a result, mRNA expression of Cxcr4, Stat3, Mapk1 and Jak2 was significantly increased in the ME group and the ME+ASX group. mRNA expression of Psen1, Notch2, Igflr, Igfl, Pi3k and Creb increased significantly only in the ME+ASX group.

4. Consideration

Here, using a microarray that can comprehensively analyze hippocampal gene expression, the molecular mechanism of the synergistic effect of the low intensity exercise and ASX effect was comprehensively analyzed, and it was to be estimated a mechanism which was different from the mechanism common with exercise alone. In the microarray experiments, gene expression of hippocampus by the low intensity exercise (ME group) for 4 weeks and a combined use of ASX uptake therewith (ME+ASX group) were screened, and IPA analysis was carried out to obtain information on gene networks, pathways and biological function.

First, before using it for microarray experiments, purity and completeness (integrity) of RNA extracted from hippocampus of each group were investigated. As a result, ribosomal RNA bands of 18 S and 28 S appeared in all the samples, and it was confirmed that the OD ratio (A260:280, A260:230) which was the purity index of RNA was 1.8 or more in all the samples.

These results show that no decomposition occur in the process of extracting RNA from the hippocampus and proved that RNA suitable for microarray analysis could be extracted. From the microarray experiments, it was found that the genes whose expression were enhanced in the ME group were to be 2,209 and the genes suppressed were 564, and the genes enhanced in the ME+ASX group were 3,891 and the genes suppressed were 411. Further, in order to estimate the molecular mechanism most accurately, IPA analysis was carried out on genes that are specifically expressed in hippocampus from past papers base. As a result, expression of Cxcr4 and Lep genes was enhanced in the ME group and the ME+ASX group in common (FIG. 9B, FIG. 10B). It has been reported that CXCR4, which is a receptor for chemokines, is involved not only in the development of granule cells of dentate gyrus in embryogenesis (Lu M, Grove E A, Miller R J. Abnormal development of the hippocampal dentate gyrus in mice lacking the CXCR4 chemokine receptor. Proc Natl Acad Sci USA 99: 7090-7095, 2002); but also contributes to improvement of spatial memory capacity (Kolodziej A, Schulz S, Guyon A, Wu D F, Pfeiffer M, Odemis V, Hollt V, Stumm R. Tonic activation of CXC chemokine receptor 4 in immature granule cells supports neurogenesis in the adult dentate gyrus. J Neurosci 28: 4488-4500, 2008). Further, CXCR4 activates the PI3K-Akt pathway and MAPK pathway to act on the survival of nerves (Chalasani S H, Baribaud F, Coughlan C M, Sunshine M J, Lee V M, Doms R W, Littman D R, Raper J A. The chemokine stromal cell-derived factor-1 promotes the survival of embryonic retinal 2003; Floridi F, Trettel F, Di Bartolomeo S, Ciotti M T, Limatola C. Signalling palthways involved in the chemotactic activity of CXCL12 in cultured rat cerebellar neurons and CHP100 neuroepithelioma cells. J Neuroimmunol 135: 38-46, 2003). In addition, administration of LEP to regulate energy expenditure promotes AHN (Garza J C, Guo M, Zhang W, Lu X Y. Leptin increases adult hippocampal neurogenesis in vivo and in vitro. J Biol Chem 283: 18238-18247, 2008), and memory loss occurs in LEP deficient animals, so that it has been clarified that LEP plays an important role in maintaining and improving hippocampal function (Li X L, Aou S, Oomura Y, Hori N, Fukunaga K, Hori T. Impairment of long-term potentiation and spatial memory in Leptin receptor-deficient rodents. Neuroscience 113: 607-615, 2002; Harvey J. Leptin regulation of neuronal excitability and cognitive function. Curr Opin Pharmacol 7, 643-647, 2007). Further, it has been clarified that LEP contributes to cell survival via JAK/STAT3 (Guo Z, Jiang H, Xu X, Duan W, Mattson M P. Leptin-mediated cell survival signaling in hippocampal neurons mediated by JAK STAT3 and mitochondrial stabilization. J Biol Chem 283: 1754-1763, 2008).

Enhancement of Stat3 gene expression by ME was confirmed by microarray analysis (FIG. 9B), and in RT-PCR, increase of Stat3 and Jak2 mRNA expression was confirmed in both the ME group and the ME+ASX group (FIG. 11). From the above findings, expression of Cxcr4 or Lep genes and downstream factors were estimated as ME and ME+ASX to be a common molecular mechanism that brings about improvement effect of AHN and cognitive function.

Interestingly, it was confirmed that the expression of Igf1r gene increased only in the ME+ASX group (FIG. 10B), and in the result of RT-PCR, the expression of Igf1r mRNA was significantly increased only in the ME+ASX group (FIG. 11).

IGF1R is a tyrosine kinase type receptor using IGF-1, IGF-2, and Insulin as a ligand (Lammers R, Gray A, Schlessinger J, Ullrich A. Differential signalling potential of insulin- and IGF-1-receptor cytoplasmic domains. EMBO J 8: 1369-1375, 1989). It has already been reported that IGF1 transfers from the blood into the brain and participates in promotion of AHN by exercise (Trejo J L, Carro E, Torres-Alemán I. Circulating insulin-like growth factor I mediates exercise-induced increases in the number of new neurons in the adult hippocampus. J Neurosci 21: 1628-1634, 2001), and participates in improvement of the spatial memory capacity controlled by the hippocampus (Sonntag W E, Ramsey M, Carter C S. Growth hormone and insulin-like growth factor-1 (IGF-1) and their influence on cognitive aging. Ageing Res Rev 4: 195-212, 2005). From these facts, the synergistic improvement effect of AHN or spatial memory capacity by combined use of ME and ASX was suggested to the possibility of participating in the downstream factor of IGF1 via IGF1R.

5. Summary

Here, in order to elucidate the molecular mechanism relating to the synergistic effect of improvement of hippocampal function by the combined use of ASX uptake and the low intensity exercise, gene expression of hippocampus was comprehensively investigated using DNA microarray, and when network analysis by IPA was carried out, the following findings could be obtained.

1) In the ME+ASX group (3,891), increase in the expression could be recognized in more genes as compared with the ME group (2,209).

2) The ME group and the ME+ASX group control the gene network related to the function of cell death and survival, and the expression enhancement of Cxcr4 and Lep gene was estimated as the common gene.

3) No change in genes was observed in the ME group, and it was revealed that the Igf1r gene, which is a receptor of IGF1 involved in nerve growth and survival, was enhanced only in the ME+ASX group.

4) According to the RT-PCR analysis, expression of mRNA of Cxcr4, Stat3, Mapk1, and Jak2 was significantly enhanced in both of the ME group and the ME+ASX group. On the other hand, significant increase in expression of mRNA of Psen1, Notch2, Igf1r, Igf1, Pi3k, and Creb was recognized only in the ME+ASX group.

Based on the above results, as a molecular mechanism which brings about a synergistic improvement effect of AHN and spatial memory by the combined use of the low intensity exercise and ASX uptake, a function mediated by IGF1R could be estimated, which is different from each single molecular mechanism.

D. General Discussion

It could be revealed that the combined use of the low intensity exercise and ASX uptake promoted AHN supporting the cognitive function carried by the hippocampus as compared with each single effect, and the spatial memory capacity is further enhanced. This was a synergistic effect that exceeded the sum of the effects of ASX uptake and the low intensity exercise alone. Further, it could be revealed for the first time that they synergistically enhance AHN and spatial memory capacity power.

The invention claimed is:

1. A method for enhancing hippocampal neurogenesis in a subject, the method comprising
performing an exercise therapy on the subject, and administering a composition comprising a carotenoid to the subject, thereby enhancing hippocampal neurogenesis, wherein the carotenoid is astaxanthin, wherein the exercise therapy is a low intensity exercise therapy, and wherein the low intensity exercise therapy is an exercise of a ventilatory work threshold value or less.

2. The method of claim 1, wherein learning function of the subject is improved.

3. The method of claim 1, wherein the astaxanthin is derived from *Haematococcus* algae.

4. The method of claim 1, wherein the administering is for at least 4 weeks.

5. The method of claim 1, wherein the composition is administered in an amount effective to upregulate at least one gene selected from the group consisting of Igflr, Lep and Cxcr4 genes.

6. The method of claim 1, wherein the composition is a medicine or a food.

7. The method of claim 1, wherein an amount of the astaxanthin administered to the subject per day is 0.5 mg to 100 mg.

* * * * *